(12) United States Patent
Baratta

(10) Patent No.: US 8,858,536 B1
(45) Date of Patent: Oct. 14, 2014

(54) DISPOSABLE MALE CATHETER SYSTEM

(71) Applicant: Joseph P. Baratta, Boca Raton, FL (US)

(72) Inventor: Joseph P. Baratta, Boca Raton, FL (US)

( * ) Notice: Subject to any disclaimer, the term of this patent is extended or adjusted under 35 U.S.C. 154(b) by 0 days.

(21) Appl. No.: 13/874,900

(22) Filed: May 1, 2013

(51) Int. Cl.
*A61M 25/00* (2006.01)
*A61M 25/02* (2006.01)

(52) U.S. Cl.
CPC .................................. *A61M 25/0074* (2013.01)
USPC ........................................................ 604/544

(58) Field of Classification Search
CPC .......... A61F 5/453; A61F 6/04; A61F 2/0054
USPC ........................................................ 604/544
See application file for complete search history.

(56) References Cited

U.S. PATENT DOCUMENTS

| | | | |
|---|---|---|---|
| 2,547,758 A | 4/1951 | Keeling | |
| 3,977,408 A | 8/1976 | MacKew | |
| 4,237,894 A * | 12/1980 | Cohen | 604/104 |
| 4,337,775 A * | 7/1982 | Cook et al. | 604/102.02 |
| 4,350,161 A * | 9/1982 | Davis, Jr. | 604/544 |
| 4,946,449 A * | 8/1990 | Davis, Jr. | 604/256 |
| 4,955,859 A * | 9/1990 | Zilber | 604/8 |
| 5,059,169 A * | 10/1991 | Zilber | 604/8 |
| 5,087,252 A * | 2/1992 | Denard | 604/346 |
| 5,474,572 A * | 12/1995 | Hayhurst | 606/232 |
| 5,571,125 A | 11/1996 | Chadwick | |
| 5,634,877 A | 6/1997 | Salama | |
| 5,919,146 A * | 7/1999 | Propp | 600/577 |
| 6,289,895 B1 * | 9/2001 | Cheng et al. | 128/885 |
| 6,349,727 B1 * | 2/2002 | Stewart, Jr. | 128/885 |
| 6,463,932 B1 * | 10/2002 | Single et al. | 128/885 |
| 6,494,855 B2 * | 12/2002 | Rioux et al. | 602/67 |
| 6,558,369 B2 * | 5/2003 | Rosenblum | 604/544 |
| 6,972,040 B2 * | 12/2005 | Rioux et al. | 623/23.66 |
| 7,926,489 B2 * | 4/2011 | Anderson et al. | 128/885 |
| 2002/0111640 A1 * | 8/2002 | Krause et al. | 606/151 |
| 2004/0173219 A1 * | 9/2004 | Bakane | 128/885 |
| 2005/0241651 A1 | 11/2005 | Rennich | |
| 2005/0256365 A1 * | 11/2005 | Timm et al. | 600/30 |
| 2008/0011310 A1 * | 1/2008 | Anderson et al. | 128/885 |
| 2009/0036729 A1 * | 2/2009 | Anderson et al. | 600/30 |
| 2010/0312226 A1 * | 12/2010 | Armistead | 604/544 |

\* cited by examiner

*Primary Examiner* — Susan Su
(74) *Attorney, Agent, or Firm* — Laurence A. Greenberg; Werner H. Stemer; Ralph E. Locher

(57) ABSTRACT

A disposable male catheter system includes a catheter to be inserted into the urethra of the penis. The catheter has a proximal end to discharge urine into a bag, a distal end to be inserted into the bladder and holes formed in the distal end to receive urine. A sleeve is disposed on and is harder than the catheter. The sleeve is slid along with the catheter within the urethra to a clamping region. A clamp is clamped over the penis at the clamping region to prevent urine from leaking around the catheter.

15 Claims, 3 Drawing Sheets

DISPOSABLE MALE CATHETER SYSTEM

BACKGROUND OF THE INVENTION

1. Field of the Invention

The invention relates to a disposable male catheter system which is commonly used to control male urinary incontinence that may be caused by different urinary problems, such as prostate cancer or stroke.

2. Description of the Related Art

Several prior art devices have been developed to control leakage or dribbling and its accompanying odor and wetness. Some of those devices include a catheter inserted into the urethra. Other catheter systems have been developed to supply medicine to the prostate and/or to withdraw fluids.

U.S. Patent Application Publication No. 2005/0241651 discloses a clamp having clamping members lined with pads and connected by a hinge and a connection pin. U.S. Pat. No. 5,571,125 similarly relates a clamp with a cushion, a hinge and quick-release screw connection. The company Bard also produces a Cunningham Clamp having a hinged steel frame with foam rubber pads and a locking device. The frame has an inwardly convex hump to add pressure to the urethra. However, it has been found that in actual use, such clamps may not adequately prevent leakage of urine all of the time.

U.S. Pat. No. 5,634,877 discloses a urine tube or catheter for urinary control on which a hydrogel collar to be placed outside the body and a balloon to be placed inside the body, are disposed. The balloon is inflated with a needle placed into an air supply tube. U.S. Pat. No. 3,977,408 provides a catheter for the injection of liquid into the prostate, having a balloon on its end and a clamp which squeezes the catheter. U.S. Pat. No. 2,547,758 discloses a cannula or catheter having a supply tube for injecting saline solution to the prostate and draining pus. Such catheter systems are either not intended to prevent urine from leaking around the catheter or do not adequately provide such prevention.

BRIEF SUMMARY OF THE INVENTION

It is accordingly an object of the invention to provide a disposable male catheter system, which overcomes the hereinafore-mentioned disadvantages of the heretofore-known devices of this general type and which prevents leakage of urine around a catheter.

With the foregoing and other objects in view there is provided, in accordance with the invention, a disposable male catheter system, comprising a catheter configured to be inserted into the urethra of the penis, the catheter having a proximal end configured to discharged urine into a bag, a distal, possibly tapered, end configured to be inserted into the bladder and holes formed in the distal end and configured to receive urine. A sleeve, preferably having beveled ends, is disposed on and is harder than the catheter and is configured to be slid along with the catheter within the urethra to a clamping region. A clamp is configured to be clamped over the penis at the clamping region to prevent urine from leaking around the catheter. The combination of the catheter, the clamp and the hard plastic sleeve on the catheter within the penis in alignment with the clamping region, prevents any leakage of urine around the catheter.

In accordance with another feature of the invention, a stopper may be slid along the catheter up to the head of the penis when the sleeve is in the clamping region. The stopper, which is used for comfort, has ridges on an outer surface thereof aiding in manual movement and fixation of the stopper in place.

In accordance with a further feature of the invention, the clamp has an outwardly convex region configured to be disposed at an area of the penis closest to the urethra, that is at the bottom, and aligned with the sleeve in the clamping region.

The force of the clamp is concentrated at the clamping region by the aligned protrusion and hard plastic sleeve, so as to stop any movement of liquid. Nevertheless, the system is comfortable to wear since the clamp need not be as tight as with prior art devices using a clamp alone that cannot concentrate the force of the clamp.

In accordance with a concomitant feature of the invention, the clamp has a living hinge, a latch to close the clamp with adjustable pressure, a rigid frame and a liner to be disposed between the rigid frame and the penis. The liner is formed of foam rubber or sponge rubber. Such features make the clamp easy to apply, adjust pressure and be quickly removable.

Other features which are considered as characteristic for the invention are set forth in the appended claims.

Although the invention is illustrated and described herein as embodied in a disposable male catheter system, it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best understood from the following description of the specific embodiment when read in connection with the accompanying drawings.

DETAILED DESCRIPTION OF THE INVENTION

Figure 1:
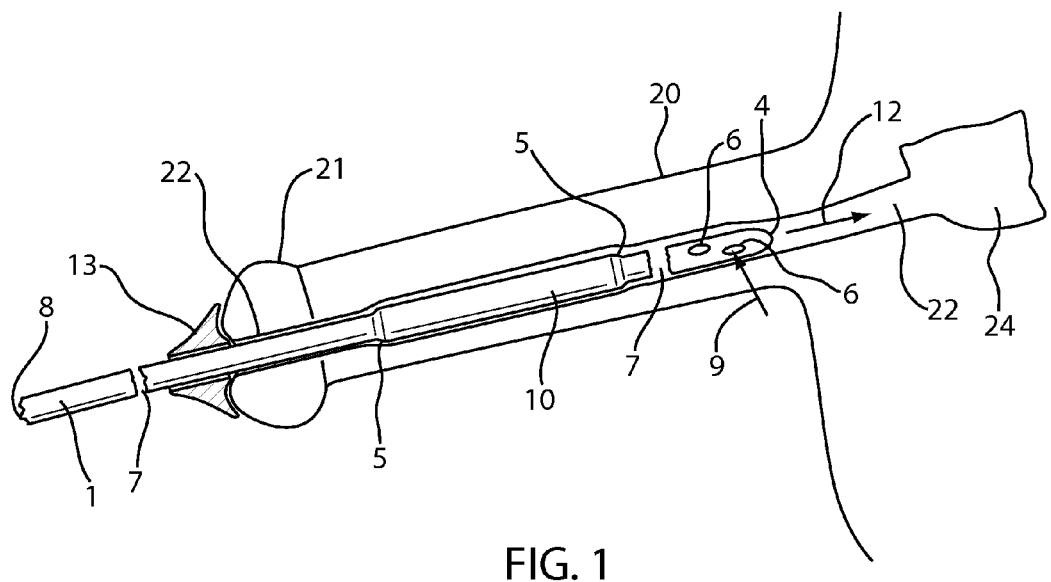
FIG. 1 is a diagrammatic, longitudinal-sectional view showing a catheter of the disposable male catheter system according to the invention during insertion.

Referring now to the figures of the drawing in detail and first, particularly, to FIG. 1 thereof, there is seen a disposable male catheter 1 in the form of a clear, flexible, plastic tube which has been partially inserted through the head 21 of the penis 20 and, more specifically, through the urethra 22 leading to the bladder 24. The catheter 1 has holes or eyelets 6 formed therein near a tapered tip or distal end 4 thereof for urine to enter from the bladder 24 as indicated by an arrow 9. A proximal end 8 of the catheter 1 leads to a non-illustrated bag, such as a urinary leg bag. The catheter 1 is somewhat flexible, but stiff enough to allow insertion. A hard plastic sleeve 10, which may be approximately three inches long, is tightly placed on the catheter 1 in such a way that it can be moved manually, but will stay in place when the catheter 1 is inserted in the direction of an arrow 12. The sleeve 10 has bevels 5 at each end for comfort during insertion and removal. A stopper 13 is placed on the catheter 1, between the plastic sleeve 10 and the proximal end 8 and, similarly to the plastic sleeve 10, can be moved manually along the catheter 1 before insertion into the urethra 22 and then to the head 21 of the penis 20, as shown in FIG. 1. The catheter 1 is longer than the length which is shown in the figure, as indicated by breaks 7.

The stopper 13 may act as a stop ring to ensure that the catheter 1 is inserted to the desired length.

Figure 2:
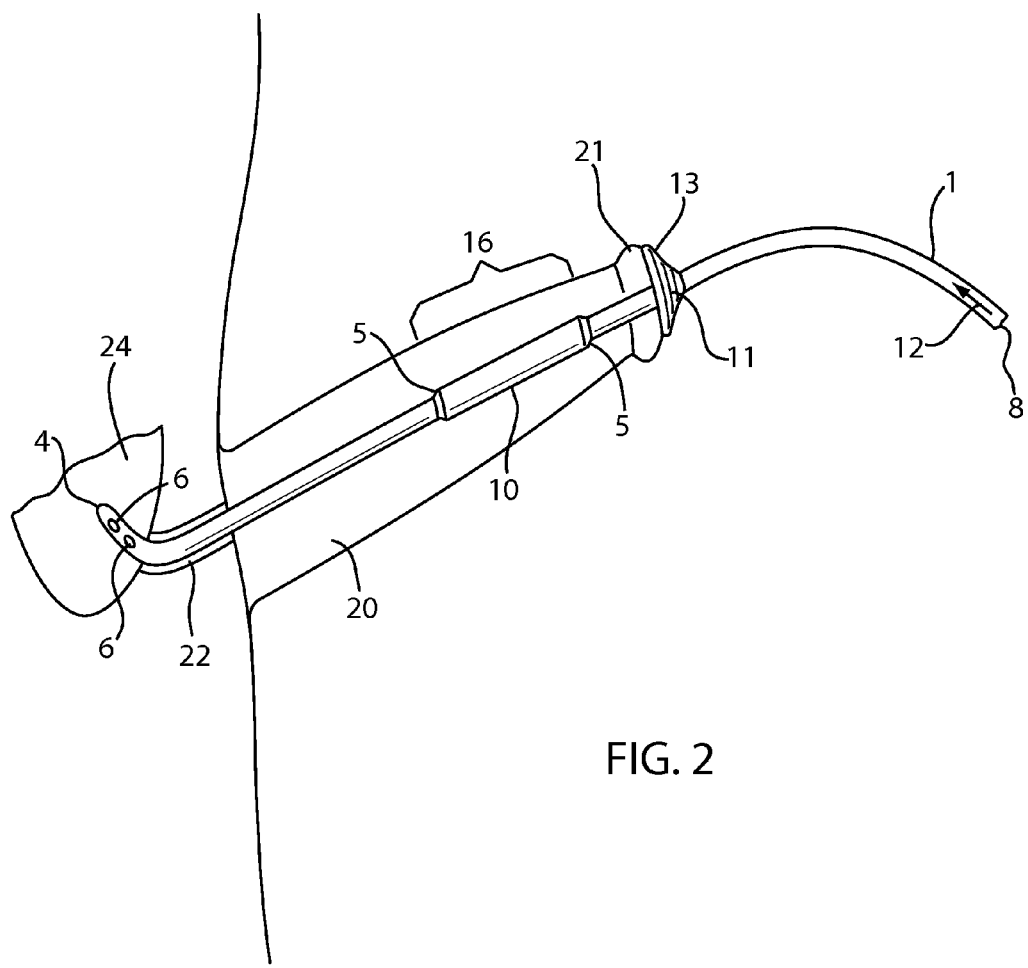
FIG. 2 is a view similar to FIG. 1 of the catheter during use.

As is seen in FIG. 2, when the catheter 1 is inserted to the correct length, the holes 6 will be disposed within the bladder 24, the plastic sleeve 10 will be located along the penis 20 at a clamping area 16 and the stopper 13 will be disposed at the head 21 of the penis 20. The stopper 13 has ridges 11 on the outside for gripping with the hand so that it can be moved and fixed in place.

Figure 3:
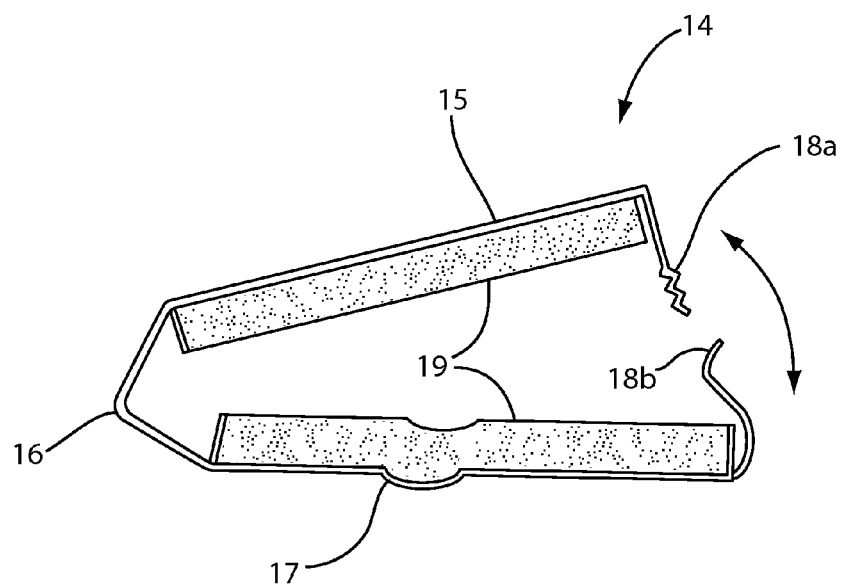
FIG. 3 is a side-elevational view of a clamp of the invention.

FIG. 3 shows a clamp 14 having a generally U-shaped steel frame 15 with a living hinge 16, a convex region in the form of a bulge or protrusion 17, an adjustable latch or locking mechanism 18a, 18b and a foam rubber or sponge rubber liner 19. The adjustable latch or locking mechanism includes a rail 18a with indentations and a finger 18b acting as a spring and having an end which may be engaged in any of the indentations to adjustably close the clamp in the direction of the curved arrow. The bulge or protrusion 17 may be placed outside the penis over the clamping area 16, which is the location of the hard plastic sleeve 10. The bulge or protrusion 17 is placed on the bottom of the penis, closest to the urethra.

Figure 4:
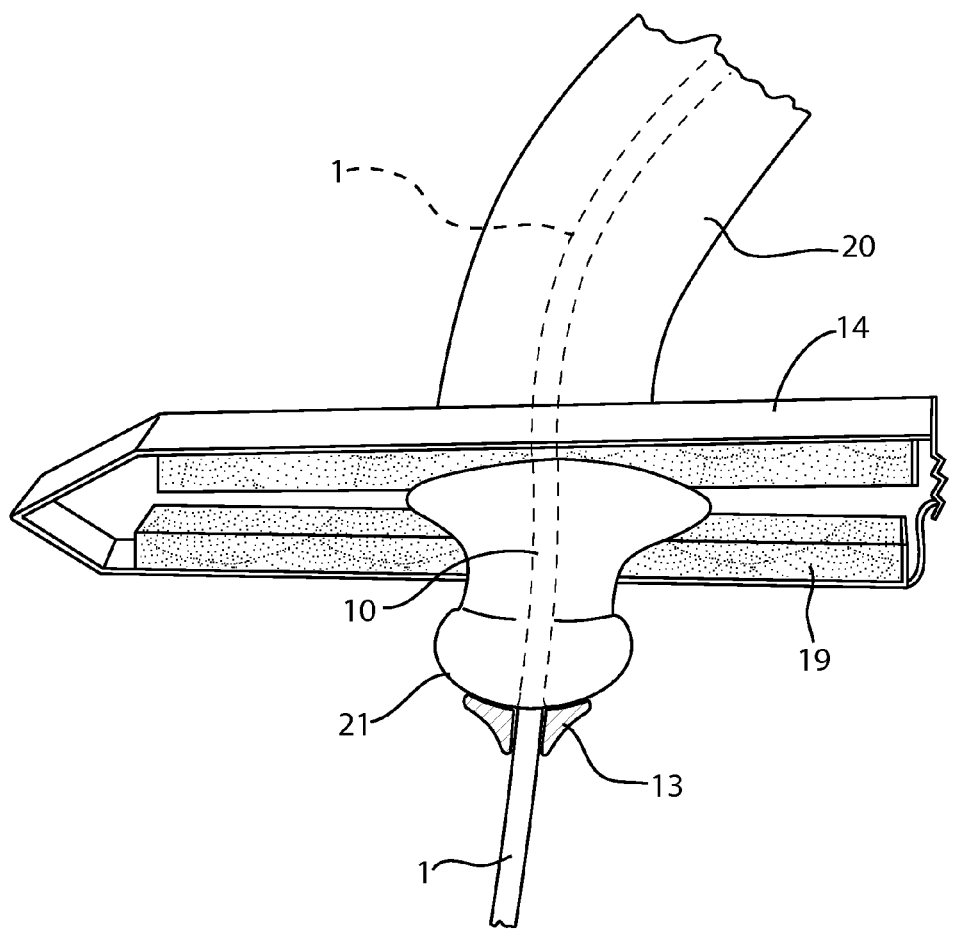
FIG. 4 is a plan view of the male catheter system after insertion and application of the clamp in a clamping area.

As is seen in FIG. 4, when the clamp 14 is closed, latched and locked around the clamping area 16, the penis 20 is clamped between the hard plastic sleeve 10 and the foam rubber pads 19 to prevent urine from leaking around the catheter 1. The stopper 13 is also moved up to the head 21 of the penis 20.

The combination of the clamp 14 and the hard plastic sleeve 10 has been found to prevent dribbling or leakage from around the catheter 1 inserted into the male urethra 22. The concentration of the clamping force provided by the aligned protrusions 17 and hard plastic sleeve 10 stop any movement of liquid and yet the system is comfortable to wear since the clamp need not be as tight as with prior art devices using a clamp alone that may not concentrate the force of the clamp. It is only necessary to squeeze a small portion of the penis because of the unique interaction of the force of the clamp 14, the protrusion 17 and the hard plastic sleeve 10, allowing urine to flow through the catheter to the leg bag without leakage.

The invention claimed is:

1. A disposable male catheter system, comprising:
    a catheter configured to be inserted into the urethra of the penis, said catheter having a proximal end configured to discharge urine into a bag, a distal end configured to be inserted into the bladder and holes formed in said distal end and configured to receive urine;
    a sleeve formed of hard material being disposed around said catheter, said sleeve being separate from and harder than said catheter, said sleeve also being configured to reside complete within the urethra and to slide along with said catheter within the urethra to a clamping region; and
    a clamp configured to be clamped over the penis at said clamping region to interact with said sleeve so as to prevent urine from leaking around said catheter.

2. The disposable male catheter system according to claim 1, which further comprises a stopper to be slid along said catheter up to the head of the penis when said sleeve is in said clamping region.

3. The disposable male catheter system according to claim 2, wherein said stopper has ridges on an outer surface thereof aiding in manual movement and fixation of said stopper in place.

4. The disposable male catheter system according to claim 1, wherein said clamp has an outwardly convex region configured to be disposed at an area of the penis closest to the urethra and aligned with said sleeve in said clamping region.

5. The disposable male catheter system according to claim 4, wherein said clamp has a living hinge.

6. The disposable male catheter system according to claim 5, wherein said clamp has a latch configured to close said clamp with adjustable pressure.

7. The disposable male catheter system according to claim 4, wherein said clamp has a rigid frame and a liner configured to be disposed between said rigid frame and the penis.

8. The disposable male catheter system according to claim 7, wherein said liner is formed of sponge or foam rubber.

9. The disposable male catheter system according to claim 1, wherein said distal end of said catheter is tapered.

10. The disposable male catheter system according to claim 2, wherein said sleeve has beveled ends.

11. The disposable male catheter system according to claim 1, wherein said hard material is hard plastic.

12. The disposable male catheter system according to claim 1, wherein said sleeve is rigid.

13. The disposable male catheter system according to claim 1, wherein said sleeve is inflexible.

14. The disposable male catheter system according to claim 1, wherein said sleeve is non-inflatable.

15. The disposable male catheter system according to claim 1, wherein said sleeve is formed of permanently hard material.

* * * * *